United States Patent [19]

Handjani et al.

[11] Patent Number: 5,079,227
[45] Date of Patent: Jan. 7, 1992

[54] PERFUME COMPOSITION, WITH A CONTINUOUS AQUEOUS PHASE, HAVING A HIGH CONCENTRATION OF PERFUME

[75] Inventors: Rose-Marie Handjani; Arlette Zabotto; Alain Ribier, all of Paris; Jacqueline Griat, Ablon, all of France

[73] Assignee: L'Oreal, Paris, France

[21] Appl. No.: 561,464

[22] Filed: Aug. 1, 1990

Related U.S. Application Data

[63] Continuation of Ser. No. 365,564, Jun. 14, 1989, abandoned.

[30] Foreign Application Priority Data

Jun. 14, 1988 [FR] France .................. 88 07911

[51] Int. Cl.$^5$ .................................. A61K 7/46
[52] U.S. Cl. ............................. 512/2; 512/3
[58] Field of Search ........................ 512/2, 3

[56] References Cited

U.S. PATENT DOCUMENTS 4,171,455 10/1979 Tomita et al. ................... 512/2
4,184,985 1/1980 Scheuermann et al. ............ 512/2

FOREIGN PATENT DOCUMENTS 0043327 6/1981 European Pat. Off. ........... 424/484
2597345 10/1987 France ......................... 424/484
57-159707 10/1982 Japan ........................... 512/2
2166107 10/1985 United Kingdom ............... 424/484

*Primary Examiner*—James H. Reamer
*Attorney, Agent, or Firm*—Cushman, Darby & Cushman

[57] ABSTRACT

A perfume composition, with an aqueous phase, having a high concentration of perfume, which contains:

a) vesicles which are obtained from at least one nonionic lipid derived from a linear or branched polyglycerol, associated with a stabilizer present in a proportion of 1 to 10% by weight based on the lipid, the vesicles having an average diameter of between 0.01 $\mu$ and 1 $\mu$ and the lipids which form the vesicles representing 0.2 to 4% by weight of the total composition; and b) a perfume in the form of droplets having an average diameter of between 0.1 $\mu$ and 1 $\mu$ and being present in the composition in amounts of between 3 and 20% by weight based on the total composition, the total ratio of the lipid or lipids of the vesicles to the perfume being between 0.05 and 0.2.

11 Claims, No Drawings

PERFUME COMPOSITION, WITH A CONTINUOUS AQUEOUS PHASE, HAVING A HIGH CONCENTRATION OF PERFUME

This is a continuation of application Ser. No. 07/365,564, filed June 14, 1989, now abandoned The present invention relates to a perfume composition, with a continuous aqueous phase, having a high concentration of perfume.

It is known that perfume compositions can take a variety of forms: they are most frequently in the form of hydroalcoholic solutions containing a high proportion of alcohol. These hydroalcoholic solutions have the advantage of being able to contain a high proportion of perfume ranging up to 25% by weight; because of the presence of alcohol, however, they irritate the skin and tend to dry it.

Perfume compositions are also known which consist of oil-in-water or water-in-oil emulsions in the form of a milk or cream. In these emulsions, the perfume is dissolved in the oil and can only be introduced in small amounts.

Finally, peptized perfumes are also prepared, but here the peptizing surfactant penetrates between the particles of perfume. In this case, the peptizing agent is likely to upset the aroma of the perfume. Furthermore, the peptizing surfactant is likely to irritate the skin and it gives the product a sticky effect.

The present invention relates to a perfume composition which does not contain a lower alcohol, but can contain a high concentration of perfume, in which the aroma of the perfume is not likely to be denatured, and which, far from irritating the skin, conversely has a soothing action on the skin by adding biomimetic lipids to the skin lipide.

The present invention relates to a perfume composition, with a continuous aqueous phase, having a high concentration of perfume, characterized in that it contains, in a continuous aqueous phase which may contain water-soluble cosmetic adjuvants:

a) vesicles which are obtained from at least one non-ionic lipid consisting of a linear or branched polyglycerol derivative of the formula

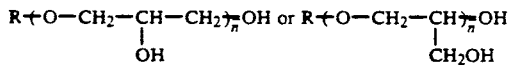

in which n has an average statistical value of between 2 and 6 and in which R can be:
1) either an aliphatic chain $R_1$ or $R_2CO$, in which $R_1$ is a linear or branched $C_{12}$–$C_{16}$ aliphatic radical and in which $R_2$ is a linear or branched $C_{11}$–$C_{17}$ aliphatic radical.
2) or a radical

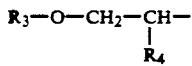

in which $R_3$ and $R_4$ are identical or different radicals $R_1$ or $R_2CO$, $R_1$ and $R_2$ being defined as indicated above, the said non-ionic lipid or lipids being associated with cholesterol when R is defined as indicated under 1) above, the said non-ionic lipid or lipids being associated with an anionic stabilizer taken from the group comprising phosphoric acid esters of $C_{12}$–$C_{22}$ fatty alcohols, lipoaminoacids and cholesterol sulphate and phosphate, the said anionic stabilizer being present in a proportion of 1 to 10% by weight based on the lipid or lipids, the vesicles having an average diameter of between 0.01μ and 1μ and the non-ionic lipid or lipids which form them representing from 0.2 to 4% by weight of the total composition; and b) a perfume containing at least one pleasant-smelling natural essential oil and/or synthetic product, essentially free from $C_1$–$C_4$ alcohol, in the form of droplets having an average diameter of between 0.1 and 1μ, the perfume being present in the composition in amounts of between 3 and 20% by weight based on the total weight of the composition, and the weight ratio of the lipid(s) of the vesicles to the perfume being between 0.05 and 0.2, it being possible for the perfume to be mixed with liposoluble cosmetic adjuvants.

It is well known that the vesicles are delimited by bimolecular or multimolecular layers of a non-ionic lipid. French patents 2 315 991 and 2 543 018 describe dispersions of lipid vesicles in an aqueous phase. French patents 2 485 921 and 2 490 504 describe that vesicles of non-ionic lipids stabilize dispersions of water-immiscible liquids, in particular oil, in an aqueous phase, without the need to add an emulsifier. The object of the present patent application is therefore to apply this property of the said vesicles to the manufacture of perfume compositions in which the droplets of perfume are kept in the form of a dispersion with the aid of the vesicles.

According to the invention, it has been found that vesicles of non-ionic lipids do not denature the aroma of the perfume used and that the presence of these non-ionic lipids, which are biomimetic compared with the skin lipids, gives the skin a better cohesion and makes the composition very soothing and pleasant to apply. The perfume composition according to the invention can therefore be used on a large area of skin without any adverse effects. The compositions according to the invention are stable on storage at room temperature; they are in the form of a slightly shiny, white milk or fluid cream which can easily be spread on the skin and they have a pleasant feel.

It has also been found that using the compositions according to the invention makes it possible to improve the retention of the perfume on the skin and therefore to extend the time for which the composition is active as a perfume.

The perfume composition can contain up to 20% by weight of perfume. It becomes difficult to obtain stable perfume compositions if the proportion of perfume exceeds 20%. The compositions according to the invention preferably contain from 5 to 16% by weight of perfume.

The non-ionic lipid or lipids of the vesicles preferably represent from 0.5 to 2% by weight.

The anionic stabilizers in the vesicles impart a negative charge to them and thereby improve their stability. The anionic stabilizers consist of phosphoric acid esters of $C_{12}$–$C_{22}$ fatty alcohols, including e.g. dicetyl or dimyristyl phosphate, lipoaminoacids which are preferably selected from those in which the acyl radical $R_5CO$—contains a $C_{13}$–$C_{19}$ hydrocarbon chain $R_5$, such as palmitoylcollagenic acid, dipalmitoyl-O,N-hydroxyprolinic acid and hydroxyproline linoleate, and cholesterol sulphate and phosphate.

The essential oils used are products obtained from starting materials of natural origin either by dry or wet steam distillation, or by mechanical processes, or by dry distillation, or by extraction with volatile solvents (see standard NF-T-75006). Examples which may be mentioned are geranium oil, bergamot oil, cedar oil, lavender oil, patchouli oil and vetiver oil. Synthetic perfume products include e.g. vanillin, linalol, phenylethyl alcohol and linalyl acetate.

According to the invention, the perfume can contain liposoluble adjuvants such as liposoluble sun filters, for example 2-ethylhexyl paradimethylaminobenzoate, substances for improving the condition of dry or senile skin, in particular unsaponifiable materials such as those derived from soya or avocado, or vitamins E and F, antioxidants or animal, vegetable, mineral or synthetic oils.

According to the invention, the aqueous phase can contain water-soluble cosmetic adjuvants such as a water-soluble dye, an opacifier, a water-soluble sun filter, a humectant such as glycerol, sorbitol, pentaerythritol, inositol or pyrrolidonecarboxylic acid or salts thereof, or a compound which is biologically active on the skin, such as a vitamin or an animal or vegetable extract.

Gelling agents may be introduced at a concentration varying between 0.1 and 2% by weight based on the total weight of the composition. In the presence of the gelling agent, a shiny fluid cream is obtained which is easy to spread on the skin and has a pleasant feel. Gelling agents which can be used include e.g. cellulose derivatives such as hydroxyethyl cellulose, derivatives of algae, such as satiagum, natural gums such as tragacanth, or a mixture of carboxyvinylic acids, such as the one marketed by GOODRICH BF under the tradename "CARBOPOL". A preservative such as methyl parahydroxybenzoate, or a pH regulator such as triethanolamine, can also be added to the aqueous phase.

The perfume composition according to the invention can be prepared in the following manner:

In a first step, a dispersion of vesicles is prepared from a non-ionic lipid or lipids containing anionic stabilizers and, if desired, cholesterol, in an aqueous phase consisting of demineralized water which may contain a humectant, a water-soluble compound which is biologically active on the skin, such as a vitamin or an animal or vegetable extract, or a preservative, using a conventional process such as the one described in French patent 2 315 991, 2 543 018 or 2 221 222.

In a second step, once the dispersion of vesicles has been prepared, the perfume is dispersed in the continuous aqueous phase. The dispersion is formed either by mechanical agitation, e.g. with an ultradisperser or a homogenizer, or by ultrasound.

The liposoluble cosmetic agents are preferably dissolved in the perfume before it is introduced into the aqueous phase. The water-soluble cosmetic agents are added to the dispersion of vesicles in the aqueous phase at the same time as the perfume or after the perfume has been dispersed. They are preferably introduced in the form of an aqueous solution.

The liposoluble and/or water-soluble cosmetic agents are preferably present in amounts of between 0.01 and 5% by weight based on the total weight of the composition.

The Examples below, which are given purely by way of illustration and without implying a limitation, provide a better understanding of the invention.

EXAMPLE 1

1st Step

In a first step, a dispersion of lipid vesicles in an aqueous phase is prepared using a non-ionic amphiphilic lipid A of the formula

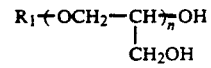

in which $R_1$ is a cetyl radical, $C_{16}H_{33}$, and $n=3$.

The following formulation is prepared:

| | |
|---|---|
| Lipid A | 0.475 g |
| Cholesterol | 0.475 g |
| Dicetyl phosphate | 0.05 g |
| Glycerol | 3 g |
| Water | 70 g |

This formulation is subjected to mechanical agitation in an ultradisperser at 40,000 rpm for 3 minutes.

Vesicles having an average diameter of $0.2\mu$ are obtained in aqueous dispersion.

2nd Step 10 g of bergamot oil (free from bergapten) are introduced into the dispersion obtained in the first step and the mixture is subjected to ultrasound for 2 minutes to give droplets of essential oil having dimensions of between 0.3 and $0.5\mu$.

An aqueous solution containing the following is then added:

| | |
|---|---|
| Methyl parahydroxybenzoate | 0.2 g |
| Water | 14.98 g |
| Polycarboxyvinylic acid marketed under the name "CARBOPOL 940" by GOODRICH | 0.42 g |
| Triethanolamine | 0.4 g |

A perfume composition having the appearance of a white cream is obtained. Its stability after storage for three months was checked.

EXAMPLE 2

1st Step

Vesicles are prepared from a mixture I consisting of 0.95 g of a non-ionic lipid B of the formula

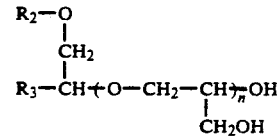

in which $R_2$ is a lauryl radical, $C_{12}H_{25}$, $R_3$ is a mixture of myristyl radicals, $C_{14}H_{29}$, and cetyl radicals, $C_{16}H_{33}$, and $\bar{n}=6$, associated with 0.05 g of an anionic agent (dimyristyl phosphate) and mixed with 8 g of demineralized water.

Using the process described in French patent 2 315 991, the vesicles are dispersed in a mixture II consisting of 61.63 g of water and 3 g of glycerol.

2nd Step

The mixture III according to Table I, consisting of a bergamot oil (free from bergapten) mixed, if desired, with perhydrosqualene, is then added. The dispersion is subjected to ultrasound for 3 minutes and a mixture IV, consisting of an aqueous solution of a polycarboxyvinylic acid sold by GOODRICH BF under the tradename "CARBOPOL", containing methyl parahydroxybenzoate and triethanolamine, is added.

Tests were carried out on the various compositions given in Table I below and the stability, in days, of the creams obtained was checked after two months at temperatures of between 4° and 45° C.

Regular topical application of any one of the three creams defined in Table I is very soothing on the user's skin and imparts a pleasant aroma.

EXAMPLE 3

A composition is prepared as in Example 2, except that the mixture IV does not contain "CARBOPOL". The composition obtained is in the form of a milk of excellent stability; topical application has the same advantages as for the creams of Example 2.

TABLE I

| Mixture | Composition | Test 1 | Test 2 | Test 3 |
|---|---|---|---|---|
| I | Lipid B | 0.95 g | 0.95 g | 0.95 g |
|  | Dimyristyl phosphate | 0.05 g | 0.05 g | 0.05 g |
|  | Demineralized water | 8 g | 8 g | 8 g |
| II | Demineralized water | 61.63 g | 61.63 g | 61.63 g |
|  | Glycerol | 3 g | 3 g | 3 g |
| III | Bergamot oil | 5 g | 10 g | 20 g |
|  | Perhydrosqualene | 5 g | 0 | 0 |
| IV | Preservative | 0.2 g | 0.2 g | 0.2 g |
|  | Demineralized water | 15.35 g | 15.35 g | 15.35 g |
|  | Carbopol | 0.42 g | 0.42 g | 0.42 g |
|  | Triethanolamine | 0.4 g | 0.4 g | 0.4 g |
|  | Stability | Good | Good | Good |

EXAMPLE 4

A perfume L corresponding to the following formulation is defined:

| | |
|---|---|
| Bergamot oil | 10 g |
| Orange oil | 6 g |
| Phenylethyl alcohol | 8 g |
| Rosewood oil | 10 g |
| α-Hexylcinnamaldehyde | 10 g |
| Condensation product of: | |
| hydroxycitronellal Schiff base and methyl anthranilate (product marketed under the name "Aurantiol" and sold by GIVAUDAN) | 8 g |
| Benzyl acetate | 5 g |
| Coumarin | 10 g |
| Heliotropin | 5 g |
| Vanillin | 5 g |
| Isomethylionone | 12 g |
| Mixture of methyl ketones obtained from treated cedar oil (product marketed under the name "VERTOFIX" and sold by "I.F.F.") | 11 g |

12 grams of the perfume L are added to the dispersion obtained at the end of the first step of Example 2 and are dispersed in the mixture; the dispersion is subjected to ultrasounds for 3 minutes and the mixture IV defined in the second step of Example 2 (see Table I) is added to the dispersion obtained. This gives a white cream which has the same stability as the cream of Example 2.

Topical application of this cream gives the same results as application of the cream of Example 2.

EXAMPLE 5

Twenty grams of the perfume L defined in Example 4 are added to the dispersion obtained at the end of the first step of Example 2. The subsequent procedure is as indicated in Example 4. This gives a white cream which has substantially the same stability and the same application properties as the cream of Example 4.

EXAMPLE 6

A perfume O corresponding to the following formulation is defined:

| | |
|---|---|
| Bergamot oil | 8 g |
| Orange oil | 8 g |
| Mandarin oil | 8 g |
| Orange Petitgrain oil | 7 g |
| Linalyl acetate | 12 g |
| α-Hexylcinnamaldehyde | 11 g |
| Patchouli oil | 6 g |
| Musk ketone | 6 g |
| Vetiver oil | 11 g |
| "VERTOFIX" product defined in Example 4 | 13 g |
| Isomethylionone | 10 g |

Five grams of the perfume O defined above and 5 grams of demineralized water are added to the dispersion obtained at the end of the first step of Example 2. A dispersion is formed and subjected to ultrasound for 3 minutes. A mixture having the following formulation is then added to the dispersion:

| | |
|---|---|
| Polycarboxyvinylic acid sold under the tradename "CARBOPOL" by GOODRICH BF | 0.2 g |
| Triethanolamine | 0.2 g |
| Methyl parahydroxybenzoate | 0.2 g |
| Demineralized water | 15.77 g |

This gives a milk which has substantially the same stability and the same topical application advantages as the milk of Example 3.

We claim:

1. A perfume composition which is soothing, pleasant to apply, easily spread on the skin and has a pleasant feel comprises in a continuous aqueous phase
   (a) vesicles obtained from at least one non-ionic lipid consisting of a linear or branched polyglycerol derivative having the formula

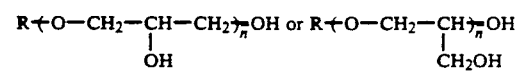

wherein
   $\overline{n}$ has an average statistical value ranging from 2 to 6, and
   R represents
   (1) an aliphatic chain $R_1$ or $R_2CO$ wherein $R_1$ is a linear or branched $C_{12}$-$C_{15}$ aliphatic radical and $R_2$ is a linear or branched $C_{11}$-$C_{17}$ aliphatic radical, or
   (2) a radical having the formula

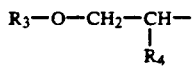

wherein
$R_3$ is $R_1$ or $R_2CO$ and
$R_4$ is $R_1$, $R_1$ and $R_2$ being identical or different and having the meanings given above,
said non-ionic lipid (a) being combined with cholesterol when R has the meaning defined in (1), above, and (b) being combined with an anionic stabilizer selected from the group consisting of a phosphoric acid ester of a $C_{12}$-$C_{22}$ fatty alcohol, a lipoamino acid having an acyl radical $R_5$—CO— wherein $R_5$ is a $C_{13}$-$C_{19}$ hydrocarbon chain, cholesterol sulfate and cholesterol phosphate, said anionic stabilizer being present in an amount ranging from 1 to 10 percent by weight based on the weight of said lipid,
said vesicles having an average diameter ranging from $0.01\mu$ to $1\mu$ and
said lipid forming said vesicles being present in an amount ranging from 0.2 to 4 percent by weight based on the total weight of said composition, and
(b) a perfume comprising one or both of a pleasant smelling natural essential oil or a synthetic product, said perfume being essentially free from a $C_1$-$C_4$ alcohol and being in the form of droplets having an average diameter ranging from 0.1 to $1\mu$,
said perfume being present in an amount ranging from 3 to 20 percent by weight based on the total weight of said composition, and
the weight ratio of said lipid forming said vesicles to said perfume ranging from 0.05 to 0.2.

2. The perfume composition of claim 1 wherein said continuous aqueous phase also contains a water-soluble cosmetic adjuvant.

3. The perfume composition of claim 1 wherein said perfume is admixed with a liposoluble cosmetic adjuvant.

4. The perfume composition of claim 1 wherein said perfume is present in an amount ranging from 5 to 16 percent by weight based on the total weight of said composition.

5. The perfume composition of claim 1 wherein said lipid forming said vesicles is present in an amount ranging from 0.5 to 2 percent by weight based on the total weight of said composition.

6. The perfume composition of claim 1 wherein said phosphoric acid ester is dicetyl phosphate or dimyristyl phosphate.

7. The perfume composition of claim 1 wherein said lipoamino acid is palmitoyl collagenic acid, dipalmitoyl-O,N-hydroxyprolinic acid or hydroxyproline linoleate.

8. The perfume composition of claim 3 wherein said liposoluble cosmetic adjuvant admixed with said perfume is at least one of a sun filter; a substance for improving the condition of dry or senile skin; an antioxidant; or an animal, vegetable, mineral or synthetic oil.

9. The perfume composition of claim 2 wherein said water-soluble cosmetic adjuvant present in said continuous aqueous phase is at least one of a dye, an opacifier, a sun filter, a humectant or a compound which is biologically active on the skin.

10. The perfume composition of claim 1 wherein said continuous aqueous phase also contains a gelling agent.

11. The perfume composition of claim 10 wherein said gelling agent is selected from the group consisting of a cellulose derivative, an algae derivative, a natural gum and a mixture of polycarboxyvinyl acids.

* * * * *